United States Patent [19]

Spandau et al.

[11] Patent Number: 5,496,733
[45] Date of Patent: Mar. 5, 1996

[54] DISCHARGE MONITORING SYSTEM

[76] Inventors: Daniel J. Spandau, 24 Ave. B, Northport, N.Y. 11768; Wayne Gutschow, 341 Charles St., Yaphank, N.Y. 11980

[21] Appl. No.: 292,746

[22] Filed: Aug. 19, 1994

[51] Int. Cl.$^6$ .................................................. G01N 35/08
[52] U.S. Cl. .................. 436/52; 422/80; 422/83; 422/89; 422/90; 422/98; 73/23.2
[58] Field of Search .................. 422/80, 83, 89, 422/90, 98; 436/52; 73/23.2, 23.35, 31.06, 1 G

[56]  References Cited

U.S. PATENT DOCUMENTS

| | | | |
|---|---|---|---|
| 2,989,143 | 6/1961 | Hallstrom | 183/2.5 |
| 4,003,257 | 1/1977 | Fletcher et al. | 73/23.1 |
| 4,113,434 | 9/1978 | Tanaka et al. | 23/232 R |
| 4,166,379 | 9/1979 | Bradshaw | 73/23 |
| 4,236,138 | 11/1980 | Segawa et al. | 338/34 |
| 4,483,824 | 11/1984 | Pink | 422/92 |
| 4,650,499 | 3/1987 | Scott | 422/89 |
| 4,892,664 | 1/1990 | Miller | 210/747 |
| 4,910,996 | 3/1990 | Pfisterer et al. | 422/89 |
| 5,250,093 | 10/1993 | Jiang et al. | 96/102 |
| 5,250,169 | 10/1993 | Logothetis et al. | 204/424 |
| 5,258,057 | 11/1993 | Baycut | 95/89 |
| 5,261,937 | 11/1993 | Jiang et al. | 96/101 |
| 5,269,935 | 12/1993 | Clough et al. | 210/653 |
| 5,273,572 | 12/1993 | Baker et al. | 93/48 |
| 5,277,056 | 1/1994 | Braun et al. | 73/23.31 |
| 5,279,145 | 1/1994 | Suzuki | 73/23.32 |

OTHER PUBLICATIONS

Combs et. al. (Design & Performance of a Sparger & Process Chromatograph for Continuous Monitoring of Volatiles in $H_2O$ at the ppb Level.) ISA 1990— Paper 90–472 pp. 527–528).
Grobaugh et. al. (Automated Analysis for Trace Organic Components in 32% Hydrochloric and 28% Hydrobromic Acid Process Streams (Analytical Chem. 50, 2, Feb. 1978, 377–379).

Primary Examiner—James C. Housel
Assistant Examiner—Sharidan Carrillo
Attorney, Agent, or Firm—Corinne R. Gorski

[57] ABSTRACT

A method and system for monitoring a concentration of volatile organic constituents in a test sample. A sparging vessel separates a volatile organic constituent sample from the test sample. A dryer dries the constituent sample to remove any vapor therein by mixing the constituent sample with a drying agent. A sorbent trap adsorbs the volatile constituents from the drying agent and concentrates the purged constituents. A microprocessor controlled director valve selectively directs the constituent sample from the dryer to the sorbent trap and from the sorbent trap to an organic vapor detector for determining the concentration of volatile constituents and for generating an electrical signal proportional to the total concentration of the volatile constituents in the sample.

24 Claims, 9 Drawing Sheets

DISCHARGE MONITORING SYSTEM

BACKGROUND OF THE INVENTION

1. Field of the Invention

The present invention relates to a discharge monitoring system for monitoring levels of volatile organic constituents (VOCs) in for example, fluids such as air streams, ground water, soils or process effluent liquids and gases, and more particularly to a monitoring system to be used on site.

2. Description of the Related Art

Groundwater contaminants, such as gasoline from leaking storage tanks and solvents from commercial/industrial waste sites, by law require remediation by the property owner. As described in U.S. Pat. No. 4,892,664, the method of clean-up generally involves the use of a water stripping tower to bring polluted groundwater to the surface in a continuous process of cleaning and recirculation back into the ground. The operation of the stripping tower system is primarily open loop with no built-in checks of the effluent water or other tower parameters to indicate proper operations after initial system installation. Government agencies regularly inspect the efficiency of the cleaning process via a water sample analysis to assure that the stripping tower effluent meets local regulatory specifications for discharge back into the water table. Should an inefficiency be identified, the property owner is liable for substantial daily fines until the condition is corrected.

It is in the property owner's best interest to know on a continuous basis the condition of the tower's effluent. However, systems presently used for this purpose are so costly to purchase, operate and maintain that only major corporations and government agencies themselves can afford to use them.

Tin-dioxide sensors have been commercially available in gas alarm applications since the early 1970s. See U.S. Pat. No. 4,236,138. Their use has been limited to high concentration detection because of the many interferences the sensors are susceptible to. These interferences include:

1) cross-sensitivity to different VOCs;
2) non-selectivity to almost any volatile organic compound;
3) temperature and humidity changes; and
4) changes in flow velocity across the sensor.

In addition to the above, the conventional tin-dioxide sensor has not been applied to analytical applications specifically for the following reasons:

1) non-linearity and low sensitivity with respect to conventional laboratory detection methods such as Flame or Photo Ionization, Electro-Chemical, Electron capture, Mass Spectrometry and other mass measuring techniques like Surface Acoustic Wave (SAW);
2) sensor drift and/or lack of long-term stability;
3) response varies from sensor to sensor, a characteristic of thick film manufacturing; and
4) the requirement of an oxygen-rich environment to operate the sensor. Most gas chromatographs operate on helium or nitrogen.

SUMMARY OF THE INVENTION

It is an object of the present invention to overcome the above deficiencies by providing a discharge monitoring system for monitoring the levels of volatile organic constituents (herein referred to as VOC's) in various samples, such as air streams, ground water, soil, process effluent liquids or gases, etc.

The discharge monitoring system of the present invention monitors a concentration of volatile organic constituents in a test sample. A sparging vessel separates a volatile organic constituent sample from the test sample. A dryer dries the constituent sample to remove any water therein by mixing the constituent sample with a drying agent. A sorbent trap separates the volatile constituents from the drying agent and concentrates the separated constituents. An organic vapor detector determines the concentration of volatile constituents and generates an electrical signal proportional to the total concentration and type of the volatile organic constituents.

The method of the present invention includes the steps of obtaining a test sample; sparging the test sample to separate a sample of volatile organic constituents from the test sample; drying the volatile organic constituent sample with a drying agent to remove any water vapor in the constituent sample; separating the volatile constituents from the drying agent to concentrate the separated volatile constituents; and detecting the concentration of the volatile constituents with a detector which generates an electrical signal proportional to the concentration and type of volatile constituents in the sample.

The monitoring system of the present invention advantageously presents a cost-effective alternative to manually retrieving samples for laboratory analysis in between the required test periods.

The monitoring system of the present invention can be connected directly to a stripping tower and provides the owner with unattended, automatic interval, on-site information as to the efficiency of the cleaning process, assuring the owner that the cleaning process is proceeding within the guidelines of the local and state government agencies while protecting the public from, for example, contaminated groundwater.

Another advantage of the monitoring system of the present invention is that, when an anomaly occurs that allows contaminants to exceed a predetermined level, the system has the capability to shut down and notify the owner or a central station of the situation.

The monitoring system of the present invention is designed to address the majority market segment that requires this technology now, but cannot afford the costs associated with Field Gas Chromatography and similar technologies costing $40,000 to over $100,000.

The monitoring system of the present invention is not designed to replace periodic mandatory testing procedures as set forth by regulators. The concept of the present invention is based on the notion that a full laboratory analysis indicating individual compounds and concentrations is not required to determine if a tower is in daily compliance. If a sample from the site can be laboratory characterized periodically for a total volatile constituent response, then a total volatile constituent limit can be calculated for use by a field deployable instrument. This type of analysis allows the use of substantially less costly detection technology.

The monitoring system of the present invention overcomes all of the limitations of conventional sensors by a unique arrangement of support hardware and software working in conjunction with a tin dioxide sensor in order to take advantage of the sensor's positive attributes: low cost, long life, rugged design, and commercial availability.

The monitoring system of the present invention utilizes a solid state tin-dioxide oxidation/reduction type sensor to provide the total organic response (go, or no-go signal) with respect to the predetermined level.

Other features and advantages of the present invention will become apparent from the following description of the preferred embodiment of the invention, which refers to the accompanying drawings.

BRIEF DESCRIPTION OF THE DRAWINGS

FIG. 11 is a cross-sectional view of the organic vapor detector of the monitoring system of the present invention.

DETAILED DESCRIPTION OF THE PREFERRED EMBODIMENT

Figure 1:
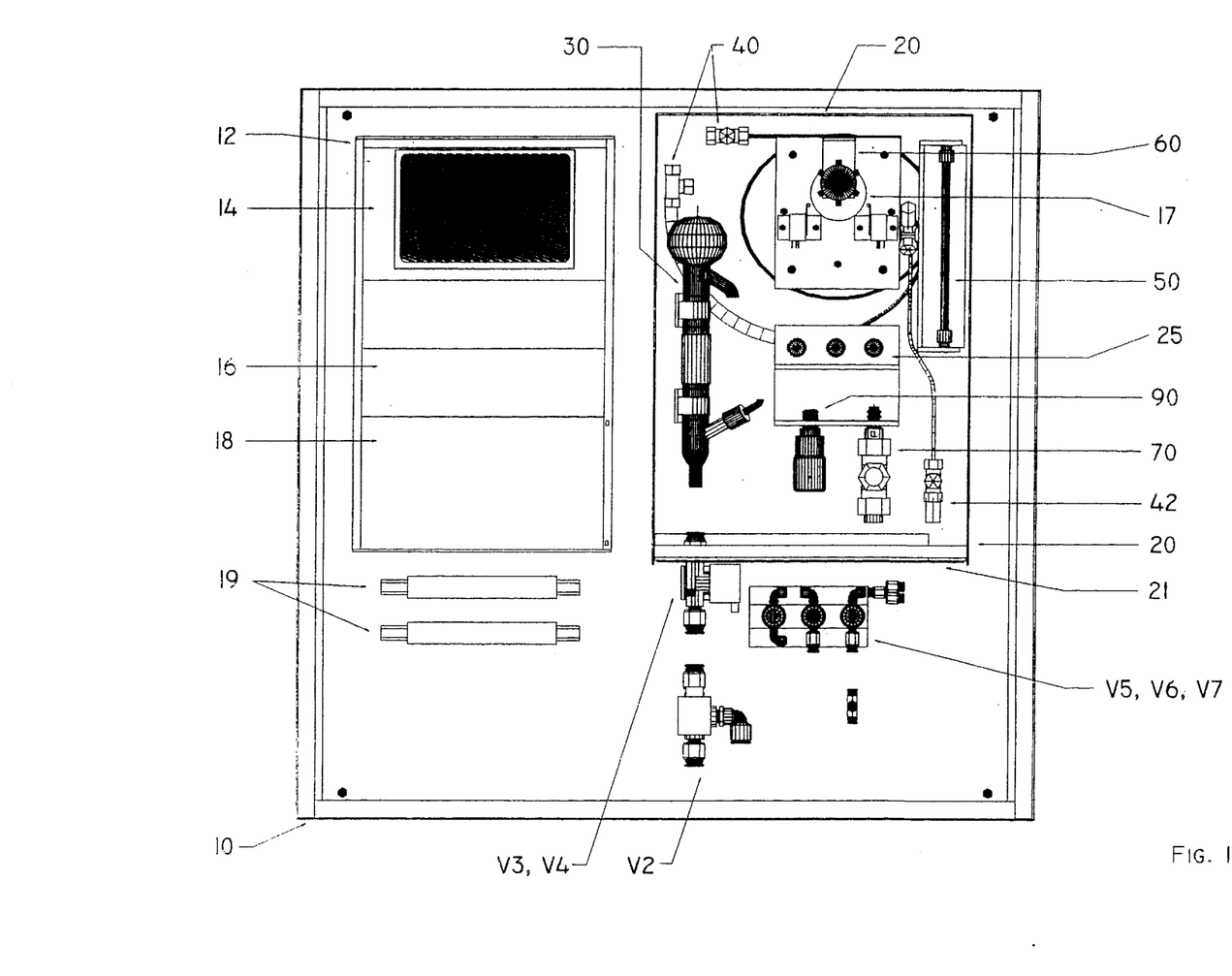
FIG. 1 illustrates the monitoring system enclosure of the present invention.

Referring to FIG. 1, the monitoring system of the present invention includes a sparging vessel 30, a first sample dryer 40, a second sample dryer 42, a director valve 60, a sorbent trap 50, an organic component detector 70 and a water vapor detector 90, all of which will be described further herein.

The entire system is microprocessor-controlled and packaged in a NEMA (National Electrical Manufacturing Association) enclosure 10 for continuous operation in hostile outdoor conditions. The ruggedized, all season design affords flexible installation considerations. Furthermore, the system has a low power consumption, less than 1000 watts @120 VAC.

The enclosure 10 allows the discharge monitoring system to be mounted outdoors, for example, next to a stripping tower or inside an equipment shed. Enclosure 10 is approximately 30×30×8 in. A door (not shown) protects the various components housed within enclosure 10.

Two compressed gas sources are supplied in weatherproof containers (not shown). Approximately 144 cubic feet of hydrocarbon free air as the carrier gas is delivered to the system through valve V5. Approximately two cubic feet of iso-butylene as the span gas is delivered to the system via valve V6. The functions of the span gas and carrier gas will be described herein.

External connections through the bottom of the enclosure are as follows:

1. One 120 VAC service connection to an internal bus bar.

2. Two ⅛" copper or stainless steel compression fit lines from the two gas storage containers.

3. One ½" water line from discharge side of stripping tower for sample collection.

4. One ½" water line for the sample drain.

5. One ½" water line for the sample overflow (may be tee'd to the sample drain external to the discharge monitor for ease of heat taping in freezing conditions).

6. Optional low voltage sensor inputs and control outputs to control stripping tower water pump, external alarms, read water flow detectors, air flow detectors and other sensors such as turbidity, pH, specific ion, et cetera.

7. Optional telephone link for modem.

Electronics module 12 separates the system controls from the wet chemistry components and protects the electronics from the environment when the enclosure door is open. The electronics module is an industry standard 19" rack turned on end to utilize available space inside enclosure 10. The rack is divided into three separate sections as follows:

The top section encloses the optional equipment module 14. This section can accommodate special measuring equipment such as turbidimeters, PH meters, specific ion probes or special controllers for external processes (i.e. chlorinators in waste water treatment plants).

The middle section 16 includes the power supplies. AC and DC power regulators provide the necessary voltages for all components in the effluent discharge monitoring system. Relays and solid state switches are located here to minimize radiating electrical noise to the microprocessor and thermocouples 19.

The lower section comprises the microprocessor and system display 18. The microprocessor contains software for sequential control of the valves and heaters of the system, interpretation of data from the detectors, communication of alarm conditions and self test and calibration routines. LED and LCD indicators display the system status for service personnel. A manual sequence step advance and master reset buttons aid in diagnostics.

Referring now to the flow diagram of FIG. 2, the monitoring process will be described briefly. The test sample is delivered to the sparging vessel 30 via line 22 and opened valves V2, V3 and V4. An optional pump (P1) is available if the test sample will not gravity feed to the vessel. Carrier gas is delivered to sparging vessel 30 via open valve V5 and gas inlet line 24. As will be described further herein, in the sparging vessel 30 the volatile constituents are separated from the test sample.

The carrier gas forces the sparged constituents from vessel 30 through line 26 into a heated primary sample dryer 40. Water vapor and interfering alcohols are selectively removed from the constituent sample by the dryer 40. The drying process will be described further herein.

The dried sample is directed toward director valve 60 and into the sorbent trap 50, where the constituents are separated from the carrier gas and concentrated in the trap media, which will be described herein. The scrubbed carrier gas exits from the trap to the atmosphere through vent or check valve 52.

The constituent sample is purged from trap 50 and directed to a secondary sample dryer 42 into organic vapor detector 70. As will be described fully herein, detector 70 generates an electrical signal proportional to the total concentration and type of volatile organic constituents present in the sample.

After the sample exits the organic vapor detector 70, it enters a water vapor detector 90 which detects fugitive traces of water vapor in the sample.

The various components of the monitoring system will now be described.

Figures 3, 4:
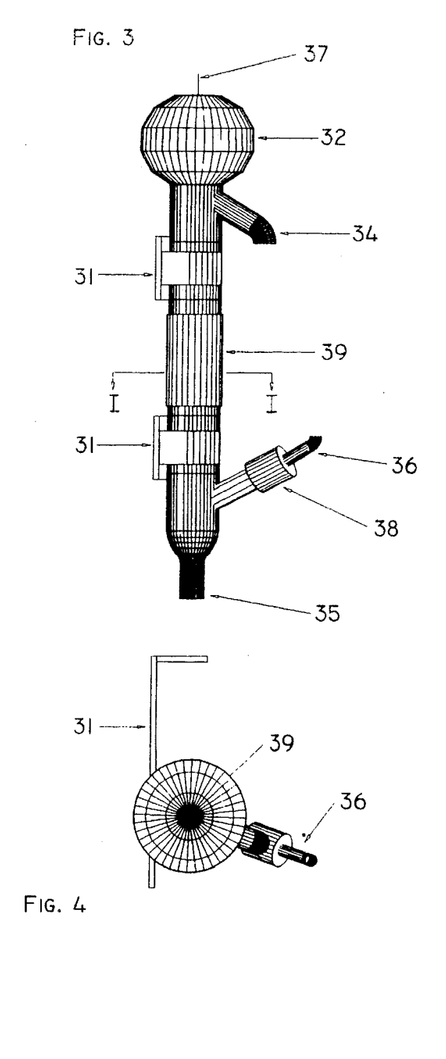
FIG. 3 is a perspective view of the sparging vessel of the monitoring system of the present invention.
FIG. 4 is a cross-sectional view of the sparging vessel taken along line I—I of FIG. 3.
Figure 5:
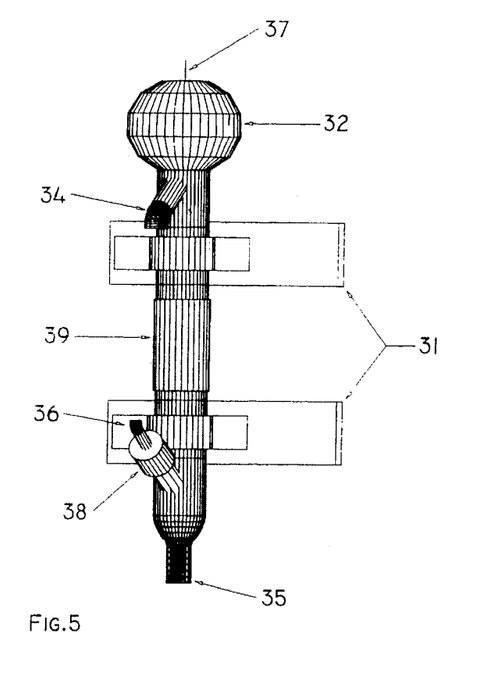
FIG. 5 is a side view of the sparging vessel of FIG. 3.

The sparging vessel 30, which separates the VOC's from the test sample, consists of a Pyrex™ tube fitted with a sphere 32 and four ports 34–37 (see FIGS. 3–5). The total interior volume of the vessel is preferably approximately 150 ml. The sparging vessel 30 is mounted in the enclosure via mounting brackets 31.

An overflow port 34 carries off all but 100 ml of the test sample when the bottom port 35 is closed, thereby providing a consistent volume for each run.

Valves V2 and V3 are fitted to the bottom port 35 to control filling and draining. Valve V4 is fitted to the overflow port 34 to allow vessel pressurization to occur when closed.

A tube fitting 38 threads into the side port 36 and supports sparging vessel 30 in the center of the tube. The threaded connector allows easy access to the diffuser assembly.

The outlet of the sparging vessel 30 includes a 60 micron sintered glass filter (not shown). The filter converts a stream of constituent free air into a widely dispersed column of fine bubbles to sparge dissolved volatile organic constituents or compounds (BTEX type —benzene, toluene, ethylbenzene and xylene) from the 100 ml test sample.

An outlet port 37 is located on the top of vessel 30 above the sample. A sphere 32 on top of the vessel dissipates bubbles that may form from, for example, detergents in the groundwater.

A heater 39 fitted to the mid-section of the tube raises the temperature of the sample from, for example, ground water temperatures to 50° C. to aid in the release of volatile constituents in the sample.

Referring back to FIG. 2, the sparged constituents are forced out of the sparging vessel outlet port 37, through line 26 into primary sample dryer 40.

Figure 6:
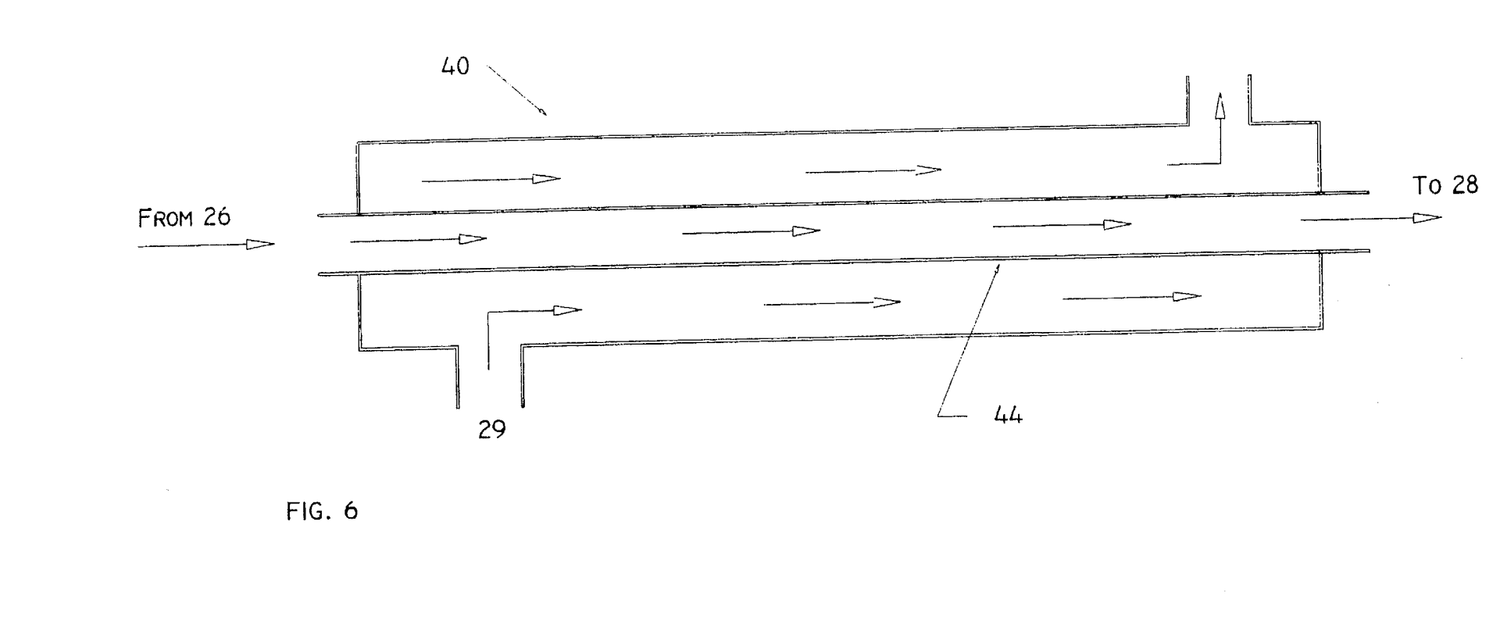
FIG. 6 is a perspective view of a sample dryer used in the monitoring system of the present invention.

Primary sample dryer 40, shown in detail in FIG. 6, selectively removes water vapor from the sample airstream prior to the organic vapor detector 70. Dryer 40 is positioned between sparging vessel 30 and directing valve 60. As shown in FIG. 2, a smaller secondary backup dryer 42 is located prior to the entry plug of the organic vapor detector 70. Valves V6 and V7 deliver the span gas to the dryers. Flow controllers 25, shown in FIGS. 1 and 2, cooperate with valves V5–V7.

The primary sample dryer 40, preferably, e.g. Model MD-050-72S manufactured by Perma-Pure Inc. of Toms River, N.J., utilizes a 72" extruded hygroscopic ion exchange membrane 44 which keeps separate the wet sample delivered via line 26 from the drying agent delivered from line 29 in a constant counter flow arrangement. The carrier gas serves as the drying agent.

If condensation were to form on the membrane of the dryer, it is likely that a water vapor breakthrough would occur. Therefore, the first six inches of dryer 40 is contained inside a molded-on custom heater (not shown) to assure that the wet sample is kept above its dew point. The rest of the dryer is coiled up in the oven compartment.

Figure 2:
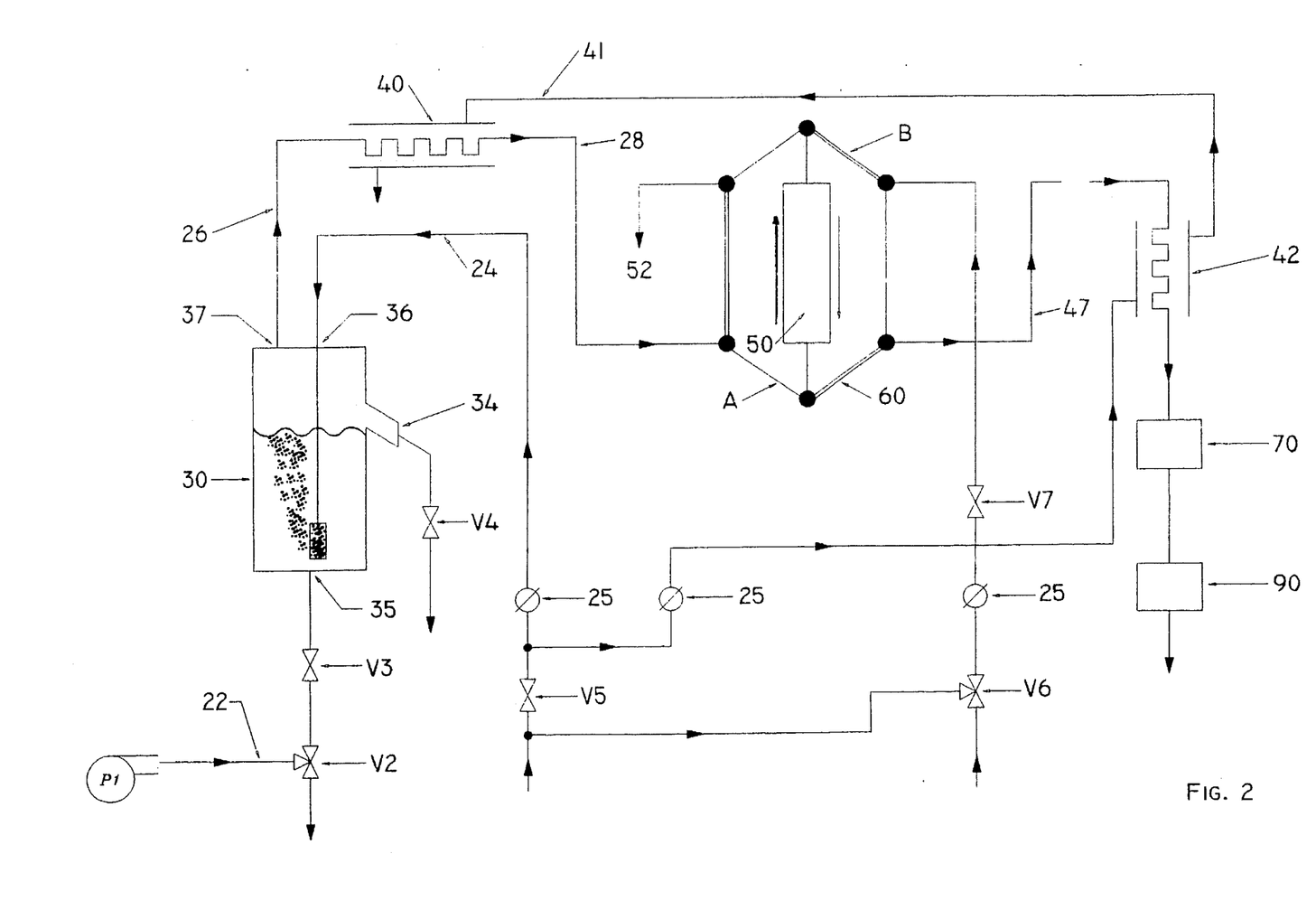
FIG. 2 is a flow diagram of the monitoring system of the present invention.
Figure 2:
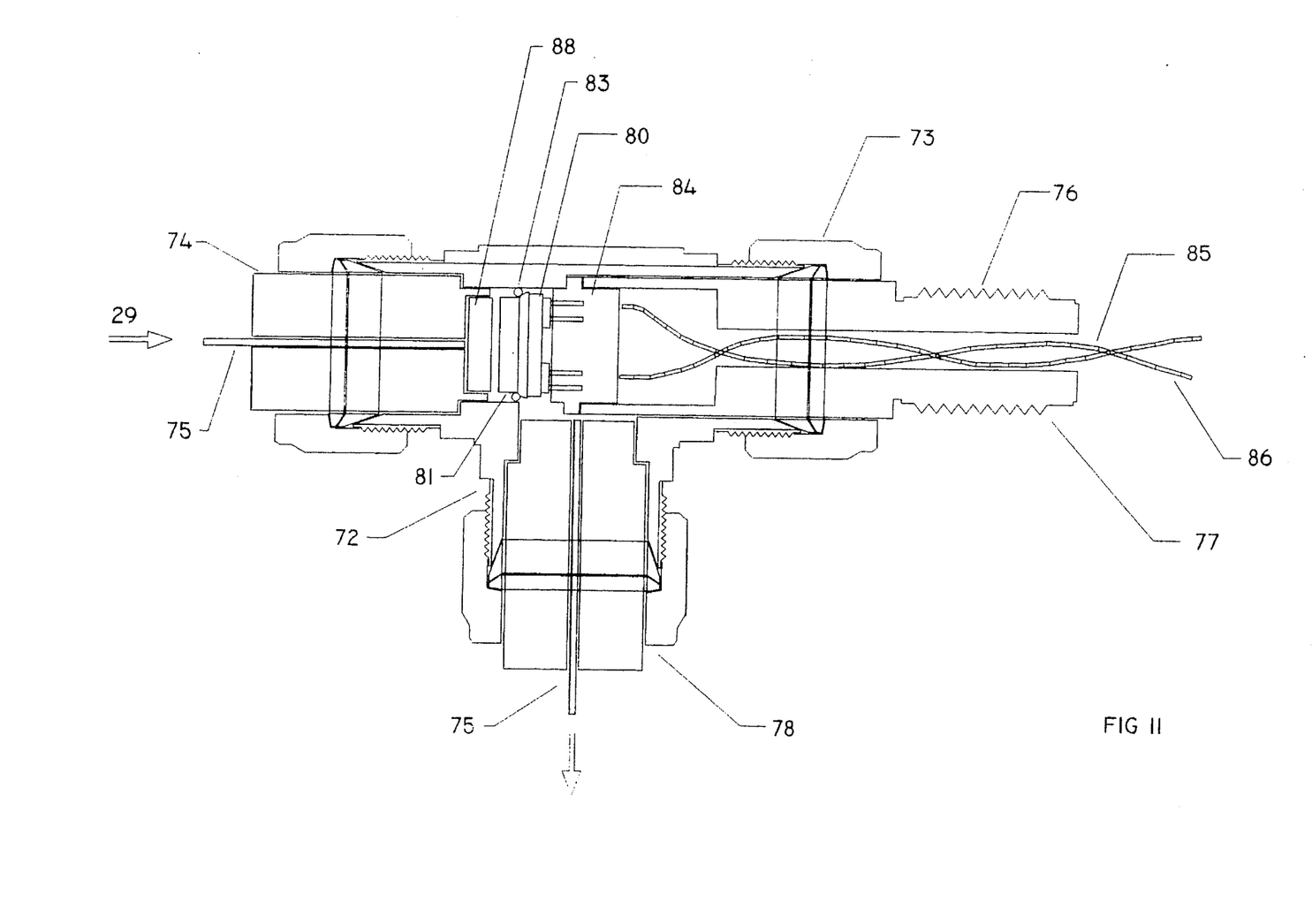

As shown in FIG. 2, the dried sample flows via line 28 to director valve 60, which controls the flow direction of the sample gas stream.

Figure 7:
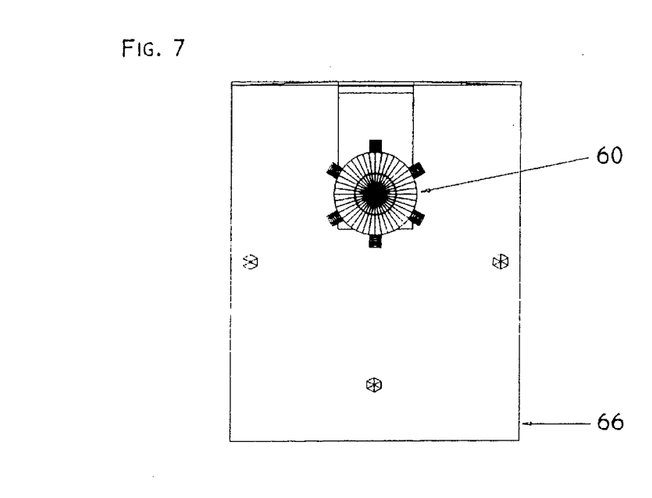
FIG. 7 is a front view of the director valve of the monitoring system of the present invention.
Figure 8:
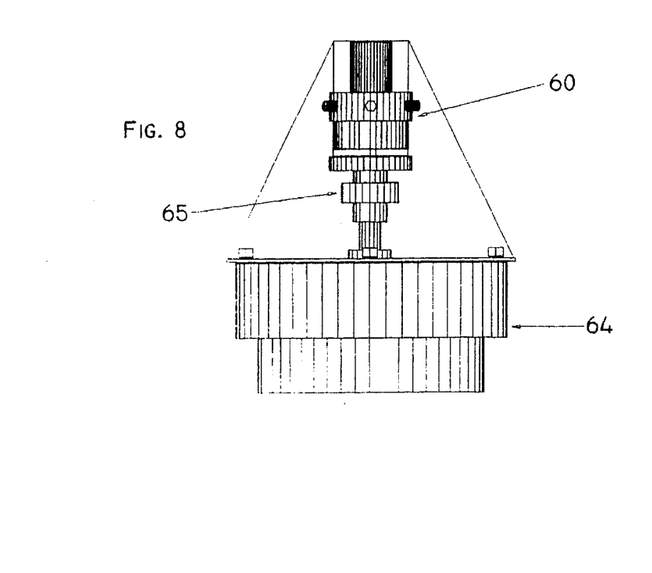
FIG. 8 is a top view of the director valve of FIG. 7.
Figure 9:
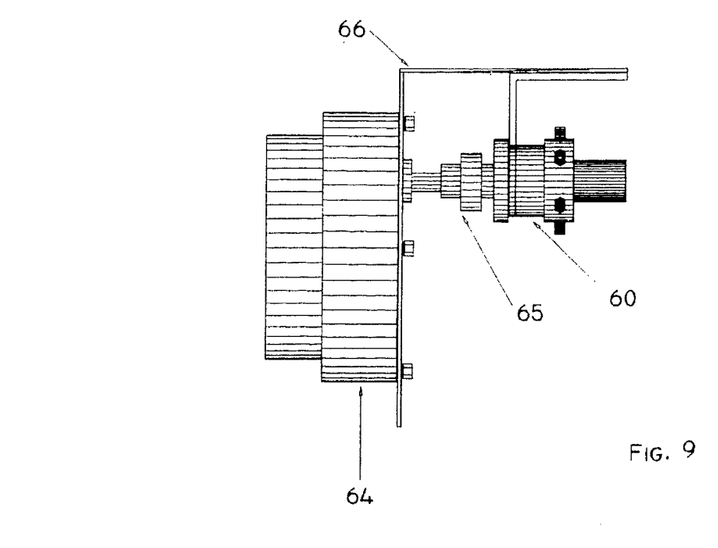
FIG. 9 is a side view of the director valve of FIG. 7.

As shown in detail in FIGS. 7–9, valve 60 is a precision six-port two position instrument valve, such as the valve manufactured by Valco Instruments Co. of Houston, Tex. The two positions shown in FIG. 2 are referred to as position (A) shown by a single line and position (B) shown by a double line. All of the discharge monitor gas sample transfer lines pass through director valve 60 to and from the various components in the system.

A DC powered pancake motor 64, via coupling 65, turns valve 60 at the appropriate times (in accordance with sequence commands from microprocessor 18) to accomplish the sparging, concentrating and purging operations. A cam and limit switch arrangement 17 (see FIG. 2) provides feedback to the computer for verification of valve movement. The director valve 60 is mounted in enclosure 10 via bracket 66.

After the dried sample flows from dryer 40 to valve 60, the valve directs the sample to sorbent trap 50 (FIG. 10) where the volatile constituents are separated from the carrier gas and concentrated in the trap media. Trap 50 concentrates the constituents sparged into the carrier gas flowstream for subsequent flash thermal desorption. Trap 50 is preferably an 8 in. long, 6 mm outer diameter hollow Pyrex tube 54 having a centerless ground with a restrictor 55 in the outlet end. A hollow tube 54 is filled with combinations of absorbable material dependant on specific target pollutant parameters. The working sites of the discharge monitoring system of the present invention are analyzed prior to installation so the sorbent trap can be filled with the appropriate material. The goal is to maximize the retention of volatile constituents in the sample while minimizing the retention of water. For initial testing, a combination of 50 mg. of Carboxen 56 and 150 mg. of Carbotrap B, manufactured by Supelco Inc., and glass wool 58 provides the concentration function of the trap. A consideration specific to the discharge monitor system is the use of air as the carrier gas with respect to the more conventional gases such as helium or nitrogen. This practice places special emphasis on the sorbent material since many materials will disintegrate at high temperatures in air. The discharge monitor temperature cycling routines have been designated to operate within the parameters of the Carboxen/Carbotrap families.

Figure 10:
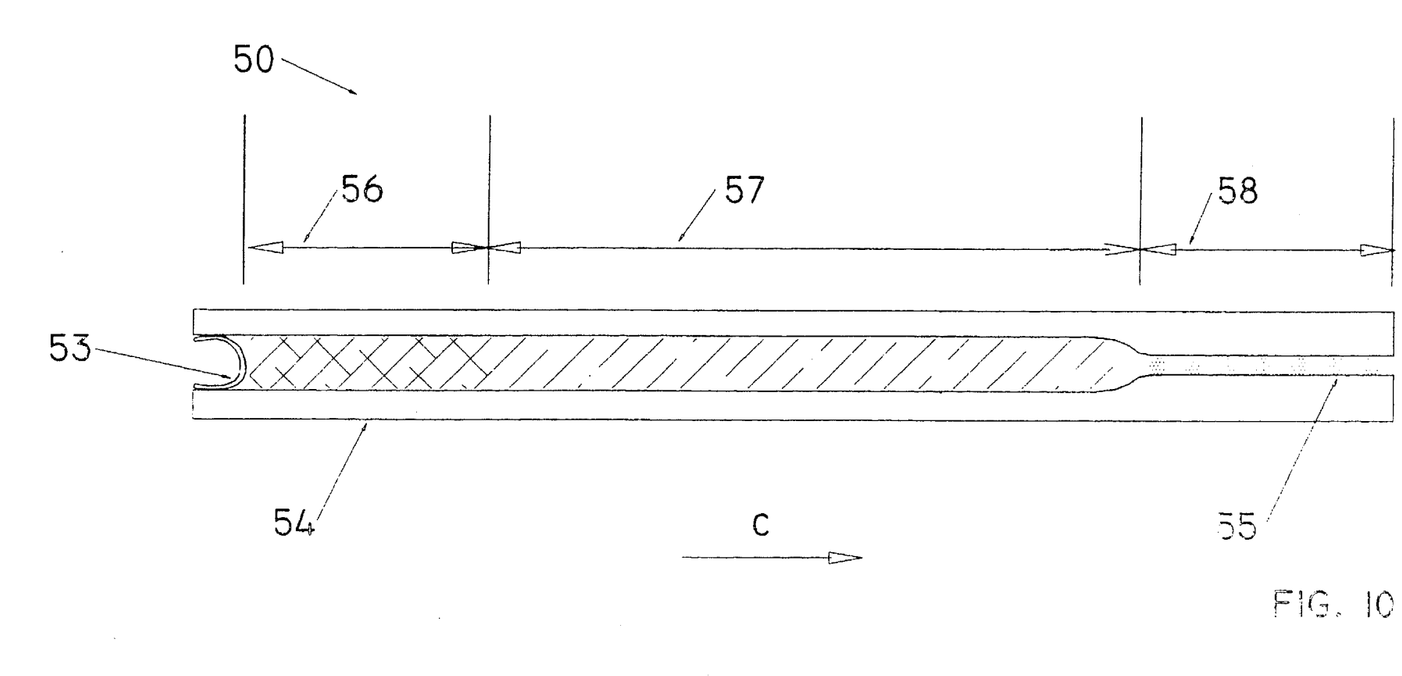
FIG. 10 is a cross-sectional view of the sorbent trap of the monitoring system of the present invention.

The sample flows through the trap in the direction shown by arrow C in FIG. 10. A 20:35 ss mesh 53 is located in the inlet end of the trap.

The trap is inserted into a sequentially controlled thermal desorption tube heater (not shown). The temperature of the trap is monitored by a pair of thermocouples to maintain a standby temperature of 50° C. Sparging and drying at 50° C. assists the hydrophobic nature of the trap medias. When the purge sequence begins, the heater momentarily climbs to 180° C. in approximately 20 seconds and then fall back to 50° C. This "flash" heat effectively places the majority of the volatilized constituents on the leading edge of the purging airstream.

As shown in FIG. 2, the volatile constituents separate from trap 50 ride with the carrier gas from line 47 through secondary sample dryer 42 into the organic vapor detector 70.

Organic vapor detector 70 generates an electrical signal proportional to the total concentration and type of VOC's in a continuous air steam.

Figure 12:
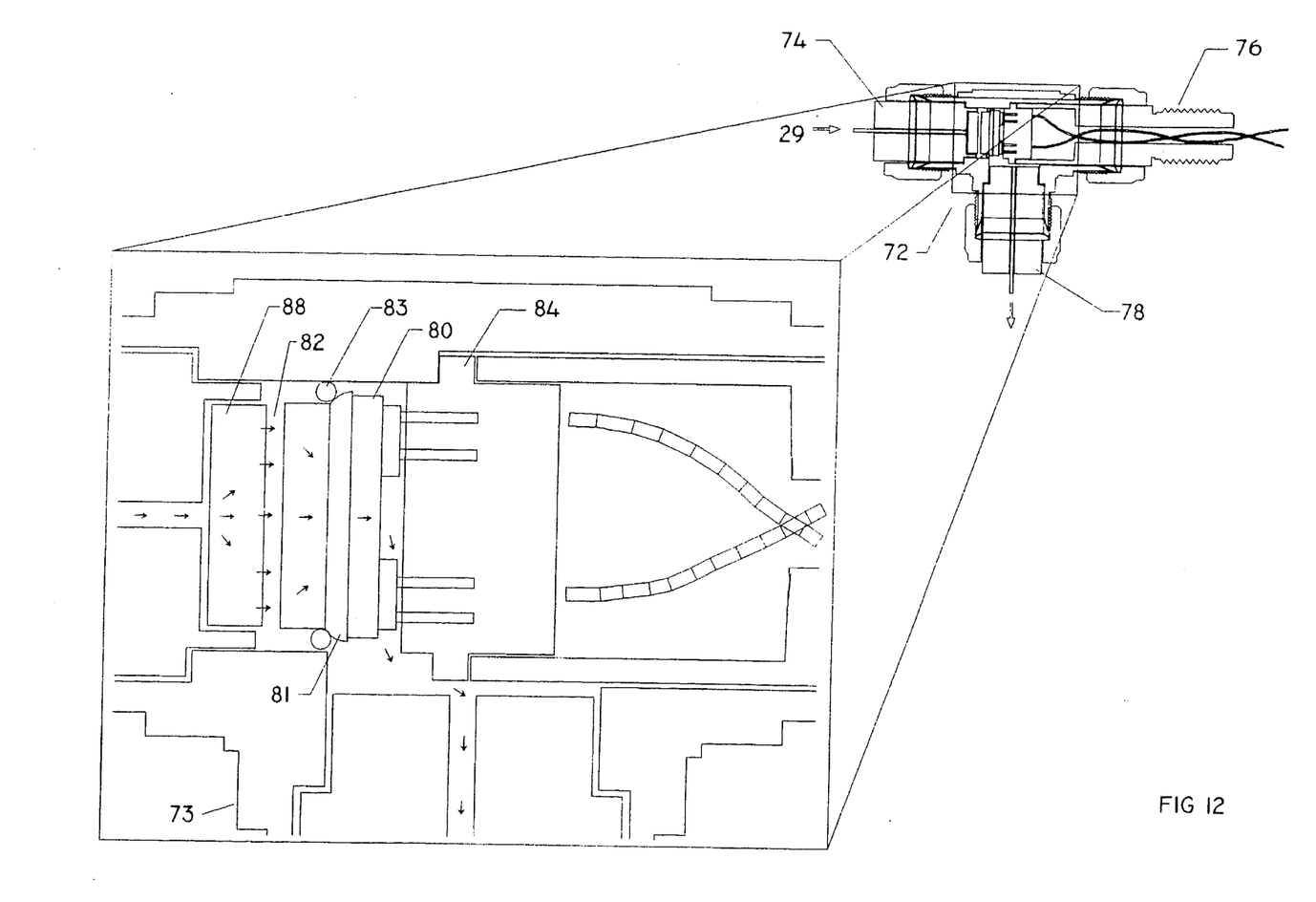
FIG. 12 is an enlarged view of the sensor element of the organic vapor detector of FIG. 11.

As shown in FIGS. 11 and 12, organic vapor detector 70 consists of a ¾" swagelok union tee 72, three custom plugs 74, 76 and 78 and a solid state sensor element 80. Locking nuts 73 secure plugs 74, 76 and 78 in tee 72. The physical arrangement of the components provides a small headspace, high velocity flow-through design.

The detection mechanism of solid state element 80 is based on the following principle. In clean air, oxygen, which traps free electrons, is absorbed onto the heated element surface 82 forming a barrier to electron flow. This creates a high resistance across sensing element 80.

When exposed to an atmosphere containing reducing gases or VOCs, the element surface 82 adsorbs the gas molecules and uses up the previously absorbed oxygen in an oxidation reaction. Electron flow is restored resulting in a lower resistance of the sensing element 80.

A highly sensitized integrated circuit (not shown) monitors the sensor resistance (and thus the rate of the oxidation reaction) and provides a non-linear signal proportional to the total concentration and type of reducing gases or VOCs present.

The sensing element 80 plugs into a socket 84 recessed permanently in the sensor support plug 76. Electrical connections are made via cables 86 extending through a centrally bored outlet port 85 (FIG. 11). The outlet port 85 is sealed airtight with an inorganic potting compound. When in place, a shoulder 81 sets the depth of the sensing element 80 such that an 0-ring 83 contacts the opposing port in the housing 73 of the tee 72.

The sample inlet plug 74 contains a nickel tube 75 brazed at the entry and exit points of the plug. A tubing extends from the inlet end to allow a union connection. A stainless steel 25 micron filter 88 is crimped at the outlet end of plug 74 to slow down and diffuse the incoming gas sample. A minimum tolerance is maintained between the filter 88 and the sensing element 80.

The sample outlet plug 78 is of the same construction as the inlet plug 74 but without a filter.

The organic vapor detector 70 assembly is located inside the isothermal oven 20 heated by heater 21 (FIG. 1) to maintain a precise temperature around sensing element 80. The outer end 77 of the sensor support plug 76 is threaded and holds the housing of the organic vapor detector 70 in place by passing through a bracket in the oven 20.

Figure 13:
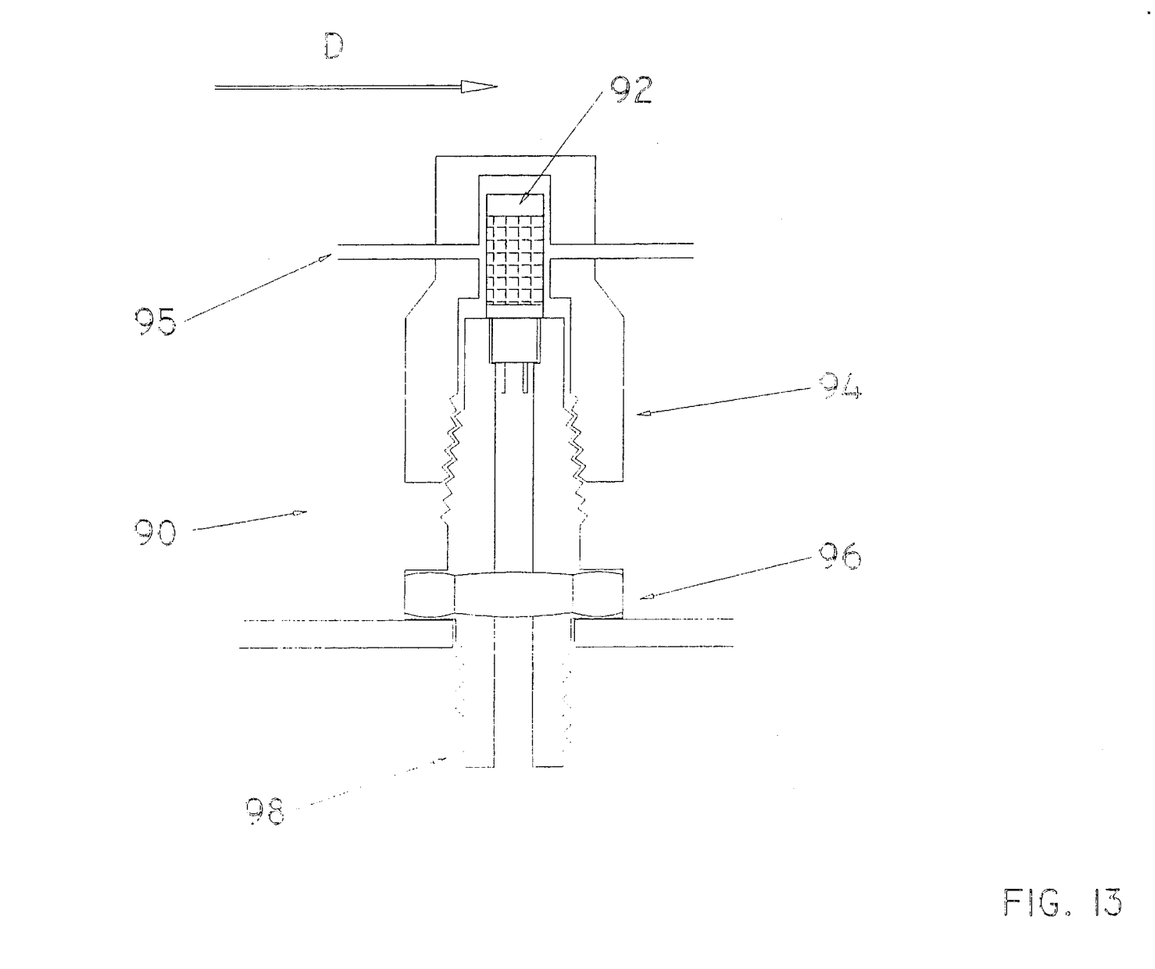
FIG. 13 is a perspective view of the vapor detector of the monitoring system of the present invention.

After the sample exits the organic vapor detector 70, it enters the water vapor detector 90, as shown by arrow D in FIG. 13. Water vapor detector 90 detects fugitive traces of water vapor in the VOC sample.

Because water vapor would create an interference in the organic vapor detector 70 output, a dedicated moisture sensor 92 constantly monitors the sample airstream. Sensor 92 is an electrically capacitive grid bonded to a water absorbing polymer, e.g. manufactured by Ohmic Instruments of Easton, Md. The sensor has a high temperature operating range and resistance to volatile organic constituent contamination.

A custom manifold 94 houses sensor 92 in a flow-through arrangement downstream of the organic vapor detector 70. Tubing 95 is brazed to housing 94. A plug 96 (swagelok ¾") accommodates sensor insert assembly 98.

The installation and calibration routine of the monitoring system of the present invention will now be described.

The first step in the discharge monitoring system installation is a laboratory analysis of the site specific and total volatile constituent characteristics using EPA method #624+ 115 for water. Based on the compounds detected, their concentration and the local allowable limits for discharge, a combined maximum allowable discharge concentration is extrapolated. This new value is then equated to a percent of response (PR) to the discharge monitor's calibrating span gas (60 ppm iso-butylene in air). The percent of response (PR) is the value the discharge monitor's computer will use to judge if a future sample is in or out of compliance.

The physical installation of the discharge monitor may be undertaken while the laboratory is analyzing the water, since the (PR) can be loaded in at the site just prior to turn-on.

When turned on, the discharge monitor starts a calibration routine and prompts for a (PR) if none has been previously entered. The (PR) will be in the form of a number that may be entered on the front panel. If a modem is used, the call number must be entered. This is the only data an installer must enter for a standard installation. All other sequence data is programmed at the factory.

The automatic calibration run time is 61 minutes. When started in automatic mode, the discharge monitor system first begins a self-calibration sequence to learn the individual characteristics of its parts and its environment. This step allows the discharge monitor to overcome many of the fallacies of tin-dioxide technology by challenging the sensor and recording the specific responses of the particular sensor it is using. The calibration sequence is automatically repeated at regular intervals.

The sequence begins with the six port valve 60 in position (B) and valves V5 and V6 allowing carrier gas to sweep all transfer lines. As the lines fill with clean carrier, the trap 50 enters a bake-out cycle at 200° C. for five minutes while water valves V2, V3 and V4 start the sparging vessel 30 on a continuous water flush. The trap 50 is cleared of any residual VOCs while the sparging vessel 30 and plumbing lines are cleared of non-associated pollutants.

In a step that assures the same quantity of test sample is sampled in each cycle, inlet valves V2 and V3 close five seconds before overflow valve V4. This allows the volume of sample flowing through the sparging vessel to top-off at the level of overflow valve V4 just prior to the vessel being sealed.

While the trap 50 undergoes a 25 minute cool down, the liquid sample is heated to the oven temperature of 51° C. and sparged to atmosphere.

This sparging process yields a purified blank liquid sample to be used in a subsequent step that duplicates an actual sample testing sequence. By substituting a blank for real sample in the sparging vessel, all associated devices from the beginning of the system to the end are evaluated and a clean wet baseline (WB) is recorded and used as a reference until the next auto calibration is performed.

The wet baseline (WB) test begins as director valve 60 moves to the concentrating position (A), see FIG. 2, placing the trap in line with the primary sample dryer 40 and sparging vessel 30. Sparging continues for 11 minutes during which time the organic vapor detector 70 is continuously exposed to clean carrier gas. At the end of 11 minutes, the output of the organic vapor detector 70 is sampled and recorded as a dry baseline value (DB).

Next, valve V3 opens and allows the carrier gas to slowly displace the blank liquid sample in the sparging vessel 30 via valve V2 and the sparge drain. This method of carrier displacement is used to empty the vessel instead of opening valves V4 and V3 together since the latter would allow atmosphere to siphon into valve V4 and contaminate the vessel as water drains from valve V3.

Valve V3 closes at a predetermined time coinciding with the emptying of the vessel. Pressure is momentarily reestablished in the system to assure that no VOCs are backed out of the trap and into the transfer lines during the sparge drain time. Director valve 60 moves to the purge position (B), now placing the trap in line with secondary sample dryer 42, organic vapor detector 70 and water vapor detector 90.

Within 15 seconds, the trap is heated to 180° C. to flash desorb any collected VOCs. Carrier gas flow moves any desorbed sample through the dryer 42 and into the organic vapor detector 70 and water vapor detector 90. When running a blank, it is common to see the organic vapor detector 70 generate a small peak corresponding to background concentrations of pollutants that build up in transfer lines and connected parts. This peak is recorded as the wet baseline (WB) value and will be subtracted from subsequent samples to yield a corrected value of total hydrocarbon response.

Director valve 60 moves back to the (A) position to sweep the organic vapor detector 70 and connecting transfer lines with clean carrier. Valve V6 opens allowing span gas to flow to dryer 42, organic vapor detector 70 and water vapor detector 90. The span gas produces a repeatable high scale reading from the organic vapor detector 70. This reading is recorded as span scale (SP). Valve V6 closes and valve 60 returns to the (B) position sweeping the remaining span gas from the system with carrier flow.

The microprocessor now has three important data points required to set up the discharge monitor's operating parameters for accurate sample testing. The percent response (PR) value that was programmed in at the start is applied to the span scale (SP) value and the resulting alarm setpoint (AS) is stored. Example:

Percent response (PR)=50% calculated

Dry baseline (DB)=1 unit measured

Wet baseline (WB)=1.5 units measured

Span scale (SP)=12 units measured

Alarm set (AS)=5.5 units calculated

Alarm set=(SP×PR)−(WB−DB)

The last test performed is a comparison of all measured and calculated values to a set of factory programmed performance windows. Each value has to fall within the minimum and maximum limit of its corresponding window for the calibration to be considered acceptable by the microprocessor. If acceptable, the program proceeds immediately to the first sample test. Unacceptable values will be discussed under "failure protocols".

The sample test monitoring process is now described with reference to FIGS. 1 and 2.

The sample test monitoring sequence begins with director valve 60 in the (B) position and a three-minute carrier gas flow to condition the trap for heating. During such sequences with timed wait states, the microprocessor calls up maintenance sub-routines that examine all of the present operating conditions of the discharge monitor system and any optional sensors connected to the stripping tower. Thermocouples 19 (FIG. 1) monitor the temperature of the isothermal oven 20, sparge vessel 30, sample dryer 40, trap 50 and electronics module 12. Pressure sensors monitor carrier and span gas tank pressures for low volume, limit switches continuously relay the present position of the 6 port director valve 60 and an IC monitors the microprocessor itself for proper operation. All data collected must conform to a preprogrammed window of operation.

The microprocessor has the ability to halt the test at any time if a failure is detected since an out of range component could cause a false alarm, as will be described herein.

Following the trap conditioning step is a 5 minute 200° C. bakeout to purge the trap 50 of any leftover VOCs from previous tests. The trap then returns to the 51° C. oven temperature during a 20 minute cool down period. The last 5 minutes of the cool down period is utilized for sparge vessel rinsing. The sparge heater 39 turns on and valves V3 & V4 open. Three way valve V2 cycles 5 times for 30 second intervals from its fill to drain position. The repetitive filling and draining action together with the bubbling of the sparge diffuser effectively rinses and prepares the vessel for the new sample. Since volatile constituents could be sparged into the transfer lines during the rinse cycle and inadvertently add to the upcoming analysis, a two-minute sealed vessel carrier sweep takes place at the end of the last empty command.

To eliminate premature constituent loss during the sample capture step, valve V5 turns off the sparging diffuser to minimize the disturbance of the incoming sample.

Valves V2, V3 & V4 open and allow the test sample to flow freely through the sparge vessel for 60 seconds. This extended flow time assures a fresh sample is carried to the discharge monitor. Valve V4 closes five seconds after valves V2 and V3 to allow the sample to top-off at the proper level in the sparging vessel.

After all three water valves are closed, director valve 60 moves to the (A) position and carrier gas valve V5 restores flow to the sparging vessel. The diffuser breaks up a 25 cc flow of carrier gas into a fine stream of bubbles to separate volatile constituents from the test sample. The process continues for 11 minutes, during which time the sparge heater raises the temperature of the sample to 51° C. to aid in the separation process.

The 25 cc diffuser gas flow forces sparged volatile constituents out of the sparging vessel port 37 through a 60 micron sintered glass filter and into the heated primary sample dryer 40. Water vapor and interfering alcohols are selectively removed from the volatile constituent sample by the counter flowing stream of carrier gas and the hygroscopic membrane.

The dried sample flows to director valve 60 and is directed to trap 50, where the volatile constituents are separated from the carrier gas and concentrated in the trap media during the 11 minute sparge period. The exit side of the trap vents the "scrubbed" carrier gas to atmosphere through a check valve 52.

A two-minute and 15 second sample discharge is initiated by opening valve V3 and allowing the diffuser gas flow to displace the sample in the sparging vessel. During this time, the microprocessor reads the organic vapor detector 70 and water vapor detector 90 to establish the dry baseline (DB). If both detectors are within acceptable windows of operation, the sequence continues.

Valve 60 moves to the (B) position in preparation to purge the constituent sample in the trap into the detectors. When the microprocessor receives the signal that 60 has completed its travel to the (B) position, a signal is sent to the heater control module to flash desorb the trap. The microprocessor monitors the peak temperature achieved by the trap and compares this to a programmed target temperature of 180° C.

As volatile constituents are purged from the trap, they ride the carrier gas through the secondary sample dryer 42 and into the organic vapor detector 70. The gas stream diffuses through the filter inside the organic vapor detector entry plug 74 and fills the sensing chamber. If volatile constituents are present, they will oxidize or reduce with oxygen previously absorbed on the sensing element 80. A peak signal will be generated and recorded by the microprocessor. The dry baseline (DB) is subtracted from this value and the difference is the sample response (SR). If the sample response (SR) is less than the alarm set value (AS), as calculated by the most recent auto calibration run, no data is recorded and the sequence continues.

After the sample exits the organic vapor detector 70, it enters the water vapor detector 90 and passes over a polymer membrane specifically sensitive to water vapor. If the humidity detector generates a signal less then a programmed set point, no data is recorded and the sequence continues to its end.

Valve V3 closes after the sparging vessel is empty, ending the two-minute and 15 second cycle, and the program enters a predetermined standby countdown to the next sample test. A typical standby cycle might be three hours, thereby providing six effluent sample tests per 24 hour period. An auto calibration sequence automatically occurs after every 25th sample test. During the standby cycle, the microprocessor continues to monitor all of the sensors in the discharge monitor and the stripping tower for system anomalies.

The discharge monitoring system of the present invention includes "failure protocols" which are a hierarchy of self-diagnostic programs that afford unattended, long-term and failsafe operation while virtually eliminating the possibility of false alarms. Two failure categories are maintained; hard failures and soft failures.

Hard failures are absolute and non-reversible. For example, low pressure in the carrier or span gas storage tank as indicated by a pressure switch, failure of the circulating pump in the stripping tower as indicated by a flow switch, out of range alarm from an accessory instrument (turbidimeter, etc.) monitored by the discharge monitor, or conclusive results of an elevated volatile constituent level in the sample discharge.

Hard failures immediately commence a "general alarm" subroutine which is programmed specifically to the end-users needs. Options for a general alarm include: indication of alarm date and nature on the control panel inside the NEMA enclosure, activation of external audible and visual annunciators, shut-down of the stripping tower operations via control relays, modem dialup to a preprogrammed telephone number or transmission of a radio signal.

Soft failures, for example, when the discharge monitor detects an out of range condition in the test sample, automatically commence a diagnostic routine that verifies the legitimacy of the condition through retests and multi-sensor analysis. A soft failure can be reliably converted to a hard failure via a programmed process of elimination.

Example: During the trap purge sequence of an sample run, the organic vapor detector 70 generates a sample response (SR) above the alarm set value (AS). A soft failure is immediately noted by the computer. A failure protocol is activated which monitors the water vapor detector 90, the next sensor the sample will encounter. If detector 90 does not signify a higher than normal indication, the program proceeds to run the full auto-calibration sequence to assure all system parameters are acceptable.

Immediately following the auto-calibration, a second sample test is run. If the last test results in the same findings as the first and all parameters are in calibration, the soft failure is advanced to a hard failure with a general alarm and the event is date-stamped and recorded.

If the water vapor detector had generated a higher than normal reading, this could indicate a dryer failure in which case water vapor could be causing the higher than normal signal in the organic vapor detector 70. The failure protocol would be slightly different in this case since the dryers may only require reconditioning by the discharge monitor. Instead of running an auto-calibration, the sample test would be reset to start over. This provides ample time for dryer reconditioning. If the second test yields an (SR) below the (AS) the original soft failure is removed from active status, date-stamped and stored in a diagnostic buffer for future review by a service technician.

This method of failure analysis provides triple protection from false alarms since any soft failure must indicate out of range readings twice plus one acceptable auto-calibration run.

The discharge monitoring system of the present invention is a multi-functional platform capable of monitoring total volatile constituents in, for example, ground water and providing closed loop control of remediation equipment for compliance assurance.

The use of a solid state type detector eliminates the cost and complications of operating a field gas chromatograph (GC), i.e., start-up cost of GC technology, exotic carrier gases, GC column replacement, specialized training required for GC operations. The discharge monitor is simple to operate and understand, inexpensive to service and is more appropriate for the purpose of monitoring total volatile constituents from a cost/performance standpoint than a GC.

The intelligent system software is a minineural net receiving data from many sources before making any alarm decisions. The system is self diagnostic and redundant, i.e., all sensors, flow switches, and thermocouples are monitored during and between sequence steps assuring system status data is always available to the computer.

Although the system of the present invention has been described in relation to the monitoring of ground water, the monitoring system of the present invention can be used to monitor various types of samples, including soils and air streams. Many other variations and modifications and other uses will become apparent to those skilled in the art. It is preferred, therefore, that the present invention be limited not by the specific disclosure herein, but only by the appended claims.

What is claimed is:

1. A discharge monitoring system located at an outdoor contaminated site, said system connected to a means for cleaning contaminated material from the contaminated site for monitoring a concentration of volatile organic constituents in a test sample obtained from said means for cleaning the contaminated site, comprising:

means for connecting the discharge monitoring system to the means for cleaning the contaminated site and for obtaining the test sample;

sparging means for separating a volatile organic constituent sample from the test sample;

means for drying the volatile organic constituent sample to remove any water therein by mixing the volatile organic constituents with a drying agent;

means for separating the volatile organic constituents from the drying agent and for concentrating the separated volatile constituents;

means for detecting the concentration of the volatile organic constituents and for generating an electrical signal proportional to the total concentration and type of the volatile organic constituents in the constituent sample; and microprocessor control means for controlling the operation of the monitoring system and automatically calibrating the system prior to monitoring the test sample, wherein a purified blank liquid sample is produced by the sparging means during the automatic calibration of the system.

2. The discharge monitoring system of claim 1, wherein the sparging means comprises a sparging vessel which receives the test sample, the separated volatile organic constituent sample being mixed with a carrier gas to force the volatile constituent sample from the vessel into the drying means.

3. The discharge monitoring system of claim 2, further comprising heating means connected with the sparging vessel for heating the test sample to aid in the separation of the volatile organic constituent sample.

4. The discharge monitoring system of claim 1, further comprising means for selectively directing the volatile organic constituent sample from the drying means to the separating means.

5. The discharge monitoring system of claim 4, wherein the directing means is controlled by the microprocessor control means; said directing means comprising a director valve which selectively directs the dried volatile organic constituent sample from the drying means to the separating means and the separated, concentrated volatile constituents from the separating means to the detecting means.

6. The discharge monitoring system of claim 5, wherein the drying means comprises a primary dryer which receives the volatile organic constituent sample from the sparging means, the director valve directing the dried constituent sample from the primary dryer to the separating means, and a secondary dryer which receives the separated, concentrated constituents from the separating means, the director valve directing the separated constituents from the separating means to the secondary dryer.

7. The discharge monitoring system of claim 1, wherein the separating means comprises a sorbent trap having a combination of different absorbable materials dependent upon specific target volatile organic constituents.

8. The discharge monitoring system of claim 1, wherein the detecting means comprises an oxidation reduction sensor.

9. The discharge monitoring system of claim 1, further comprising water vapor detecting means in communication with the means for detecting the concentration of the volatile organic constituents, the water vapor detecting means detecting traces of water vapor in the volatile constituents.

10. The discharge monitoring system of claim 1, wherein the drying agent comprises a carrier gas.

11. The discharge monitoring system of claim 10, wherein the carrier gas is air.

12. A method of monitoring a concentration of volatile organic constituents in a test sample obtained from an outdoor contaminated site with a monitoring system located at the outdoor contaminated site and connected to means for cleaning contaminated material from the contaminated site, comprising the steps of:

connecting the monitoring system to the means for cleaning the contaminated site;

obtaining a test sample of the contaminated material from the contaminated site;

automatically calibrating the monitoring system to produce a purified, liquid blank sample in a sparging vessel of said monitoring system and using said liquid blank sample to calibrate the system prior to analysis of said test sample;

separating a sample of volatile organic constituents from the test sample in said sparging vessel;

drying the volatile organic constituent sample with a drying agent to remove any vapor in the constituent sample;

separating the volatile constituents from the drying agent to concentrate the volatile organic constituents of the constituent sample;

detecting the concentration of the volatile organic constituents by detecting means which generates an electrical signal proportional to the concentration and type of the volatile organic constituents in the constituent sample; and determining if the volatile organic constituents concentration of said test sample is within a predetermined value generated by the microprocessor control means of the monitoring system.

13. The method of claim 12, wherein prior to the step of obtaining the test sample, volatile organic constituent characteristics of the site are analyzed, the constituents present are detected and the concentration of the constituents detected are input into the microprocessor control means as a percentage of response value (PR).

14. The method of claim 13, wherein the purified blank liquid sample is produced by continuously flushing said monitoring system with water and sparging said water in the sparging vessel to produce said purified blank liquid sample, wherein said blank liquid sample is used as a reference sample in the system, and an output signal of the detecting means corresponding to background concentrations of pollutants in the system is recorded by said microprocessor control means a wet baseline value (WB).

15. The method of claim 14, wherein prior to the step of obtaining the test sample, the detecting means of the monitoring system is exposed to clean carder gas, an output signal of the detecting means is sampled and the output signal of said detecting means is recorded by said control means as a dry baseline value (DB).

16. The method of claim 15, further comprising the step of sweeping the system with a span gas and exposing the detecting means to the span gas and recording an output signal of the detecting means by said microprocessor control means as a span scale value (SP).

17. The method of claim 16, further comprising the step of determining an alarm setpoint value (AS) from the following equation:

$$(AS)=(SP \times PR)-(WB-DB)$$

wherein, the alarm setpoint value (AS) is a value said microprocessor control means uses to determine if the constituent concentration in the test sample is within said predetermined value.

18. The method of claim 12, wherein the step of sparging comprises delivering the test sample to the sparging vessel, mixing a carrier gas with the test sample to separate the volatile organic constituent sample therefrom, and forcing the sparged constituent sample from the sparging vessel into a sample dryer.

19. The method of claim 18, wherein, in the step of drying, the dryer separates water vapor from the constituent sample by a counterflowing stream of carrier gas.

20. The method of claim 19, further comprising the step of directing the dried constituent sample from the dryer to a sorbent trap by a director valve controlled by a microprocessor of the monitoring system.

21. The method of claim 20, wherein the step of separating comprises separating the volatile constituents from the carrier gas, and flash heating the sorbent trap to concentrate the volatile organic constituents.

22. The method of claim 21, further comprising the step of directing the separated volatile constituents from the sorbent trap into the detecting means.

23. The method of claim 12, further comprising the step of detecting traces of water vapor in the volatile constituents after the step of detecting the concentration of the constituents.

24. The method of claim 17, wherein the detecting means detects the amount of volatile organic constituents present in the test sample and generates a peak signal which is recorded by the microprocessor control means as a sample value, the microprocessor subtracts the dry baseline (DB) from said sample value and the difference is recorded as a sample response (SR), and further comprising the step of comparing the sample response (SR) with the alarm setpoint value (AS) to determine if the sample response value is greater than the alarm setpoint value.

* * * * *

UNITED STATES PATENT AND TRADEMARK OFFICE
CERTIFICATE OF CORRECTION

PATENT NO. : 5,496,733
DATED : March 5, 1996
INVENTOR(S) : SPANDAU et al.

It is certified that error appears in the above-indentified patent and that said Letters Patent is hereby corrected as shown below:

Column 14, claim 15, line 24, delete "carder", insert --carrier--; line 26, before "control" insert --microprocessor--.

Signed and Sealed this

Twenty-third Day of July, 1996

Attest:

BRUCE LEHMAN

*Attesting Officer*  *Commissioner of Patents and Trademarks*